(12) United States Patent
Nervo et al.

(10) Patent No.: US 11,839,888 B2
(45) Date of Patent: Dec. 12, 2023

(54) SYSTEM AND METHOD FOR DISPENSING A MIXTURE OF A LIQUID AND AN ADDITIVE AND CARTRIDGE FOR USE THEREIN

(71) Applicant: DISPENSING TECHNOLOGIES B.V., Eindhoven (NL)

(72) Inventors: Paulo Nervo, Hoogeloon (NL); Dennis Van Melick, Eindhoven (NL); Dominicus Jan Van Wijk, Helmond (NL)

(73) Assignee: DISPENSING TECHNOLOGIES B.V., Eindhoven (NL)

( * ) Notice: Subject to any disclaimer, the term of this patent is extended or adjusted under 35 U.S.C. 154(b) by 0 days.

(21) Appl. No.: 17/295,650

(22) PCT Filed: Nov. 26, 2019

(86) PCT No.: PCT/EP2019/082642
§ 371 (c)(1),
(2) Date: May 20, 2021

(87) PCT Pub. No.: WO2020/109341
PCT Pub. Date: Jun. 4, 2020

(65) Prior Publication Data
US 2022/0001407 A1    Jan. 6, 2022

(30) Foreign Application Priority Data

Nov. 26, 2018    (NL) ..................................... 2022072

(51) Int. Cl.
*B05B 11/00*    (2023.01)
*B65D 81/32*    (2006.01)
(Continued)

(52) U.S. Cl.
CPC ........ *B05B 11/0054* (2013.01); *B05B 1/3006* (2013.01); *B05B 9/0833* (2013.01);
(Continued)

(58) Field of Classification Search
CPC . B05B 11/0054; B05B 1/3006; B05B 11/007; B05B 11/0081; B05B 11/001;
(Continued)

(56) References Cited

U.S. PATENT DOCUMENTS 3,966,089 A * 6/1976 Klingaman ............... B67B 7/28
222/88
4,201,316 A * 5/1980 Klingaman ........ B65D 81/3222
222/80
(Continued)

FOREIGN PATENT DOCUMENTS

WO    2007107778 A1    9/2007
WO    2016106457 A1    7/2016

OTHER PUBLICATIONS

International Search Report and Written Opinion for the International Patent Application No. PCT/EP2019/082642, dated Mar. 20, 2020, 13 pages.

*Primary Examiner* — Frederick C Nicolas
(74) *Attorney, Agent, or Firm* — KDW FIRM PLLC

(57) ABSTRACT

A liquid dispensing system includes at least one container for storing the liquid to be dispensed, the at least one container having a neck defining a fill opening for the liquid. The system includes a liquid dispensing device releasably connectable to the at least one container, an exchangeable cartridge for an additive to be mixed with the stored liquid, where the cartridge is accommodated in the neck, and a piercing member for opening the cartridge. The cartridge includes a one-piece hollow body filled with the additive and with a pressurized gas, and the piercing member is arranged to pierce a wall of the hollow body. A method of dispensing a liquid by using the liquid dispensing system, and a cartridge for use in the liquid dispensing system and/or method.

20 Claims, 10 Drawing Sheets

(51) Int. Cl.
   *F16K 15/14*   (2006.01)
   *B05B 1/30*    (2006.01)
   *G01F 11/08*   (2006.01)
   *B05B 9/08*    (2006.01)
   *B05B 11/10*   (2023.01)
   *B05B 11/04*   (2006.01)
   *F16K 21/00*   (2006.01)
   *A61M 5/20*    (2006.01)
   *F16K 15/18*   (2006.01)

(52) U.S. Cl.
   CPC ........ *B05B 11/007* (2013.01); *B05B 11/0081* (2013.01); *B05B 11/047* (2013.01); *B05B 11/104* (2023.01); *B05B 11/1077* (2023.01); *B65D 81/3222* (2013.01); *F16K 15/141* (2013.01); *F16K 15/142* (2013.01); *F16K 21/00* (2013.01); *G01F 11/08* (2013.01); *A61M 5/2053* (2013.01); *A61M 2005/2013* (2013.01); *B05B 11/001* (2013.01); *B05B 11/1011* (2023.01); *F16K 15/1825* (2021.08)

(58) Field of Classification Search
   CPC ... B05B 11/304; B05B 9/0833; B05B 11/047; B05B 11/3077; B05B 11/3011; B05B 11/1011; B05B 11/1077; B05B 11/104; B65D 81/3222; F16K 15/142; F16K 15/141; F16K 15/1825; F16K 21/00; A61M 5/2053; A61M 2005/2013; G01F 11/08
   See application file for complete search history.

(56) References Cited

U.S. PATENT DOCUMENTS

| | | | |
|---|---|---|---|
| 4,613,061 A | | 9/1986 | Meuresch et al. |
| 4,679,706 A | * | 7/1987 | Magid .................. B65D 83/625 222/402.18 |
| 4,772,326 A | * | 9/1988 | Heinen .................. C04B 28/34 106/695 |
| 5,018,643 A | * | 5/1991 | Bolduc ................ B65D 83/687 222/129 |
| 5,064,121 A | * | 11/1991 | Bolduc ................ B65D 83/687 239/309 |
| 5,256,723 A | * | 10/1993 | Hense .................. C08F 220/16 525/445 |
| 5,836,479 A | * | 11/1998 | Klima ................ B05B 11/0097 222/83.5 |
| 5,871,122 A | * | 2/1999 | Klima ................ B05B 11/0086 222/130 |
| 5,947,332 A | | 9/1999 | Klima, Jr. et al. |
| 7,909,210 B2 | * | 3/2011 | Roth .................. B65D 51/2835 222/145.5 |
| 8,157,131 B2 | * | 4/2012 | Sim ..................... B05B 11/0081 222/129 |
| 8,261,943 B2 | * | 9/2012 | Sim ..................... B05B 11/0056 222/129 |
| 8,302,816 B2 | * | 11/2012 | Sim ..................... B05B 11/0056 222/129 |
| 8,336,733 B2 | * | 12/2012 | Laws .................. B01F 35/7162 222/399 |
| 9,764,342 B2 | * | 9/2017 | Vellutato, Jr. ............. A61L 2/22 |
| 9,809,437 B2 | * | 11/2017 | Tansey, Jr. ........... B67D 1/0051 |
| 2005/0223904 A1 | * | 10/2005 | Laigneau ............ A47J 31/3695 206/0.5 |
| 2016/0137402 A1 | * | 5/2016 | Talon .................. B65D 85/8055 426/115 |

* cited by examiner section IV-IV

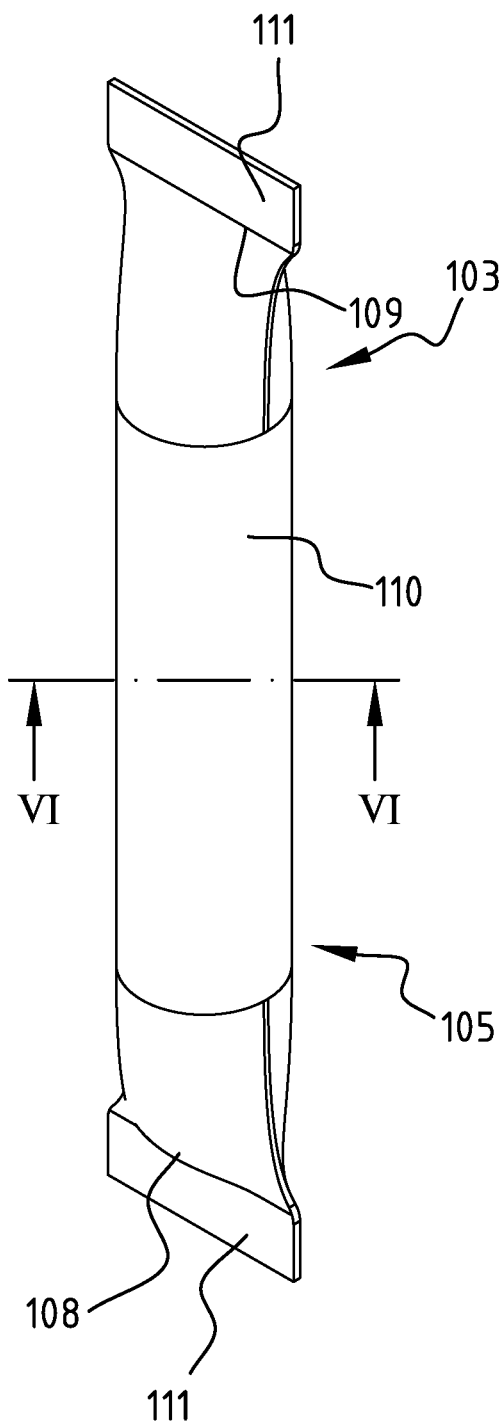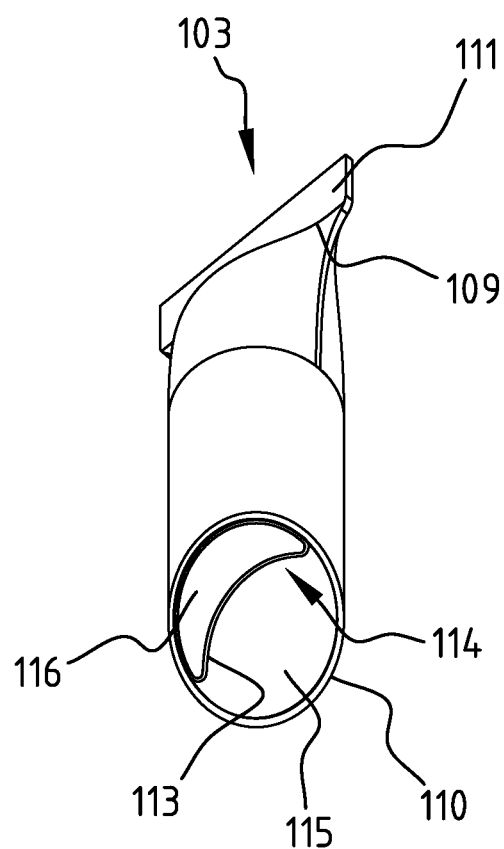
FIG. 5
FIG. 6

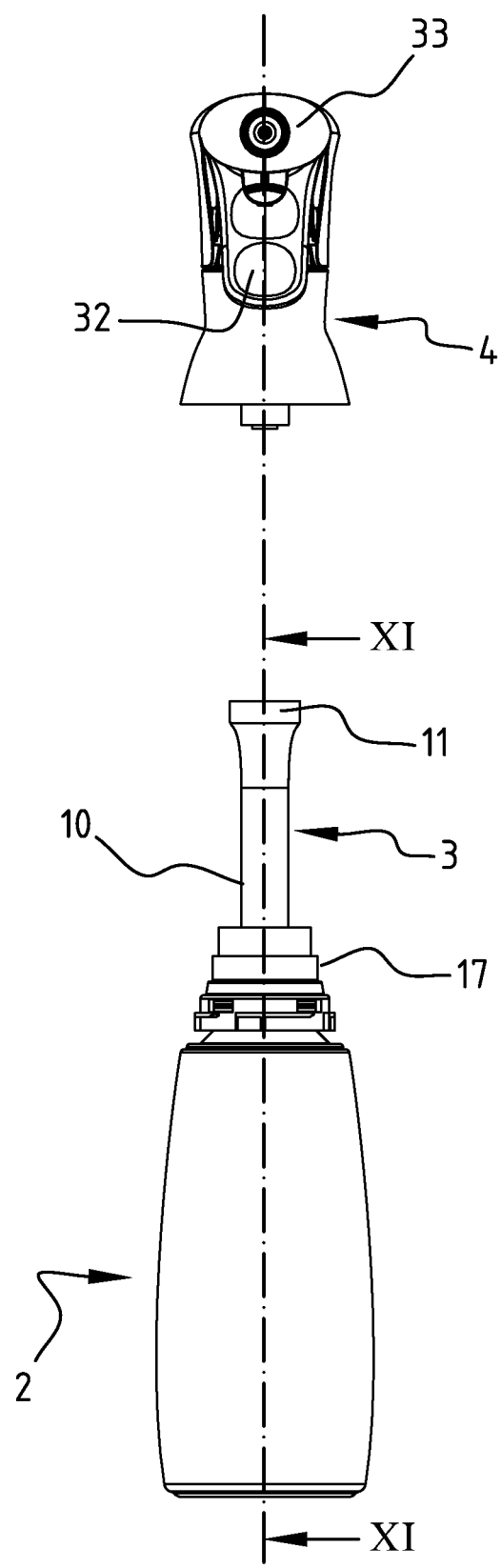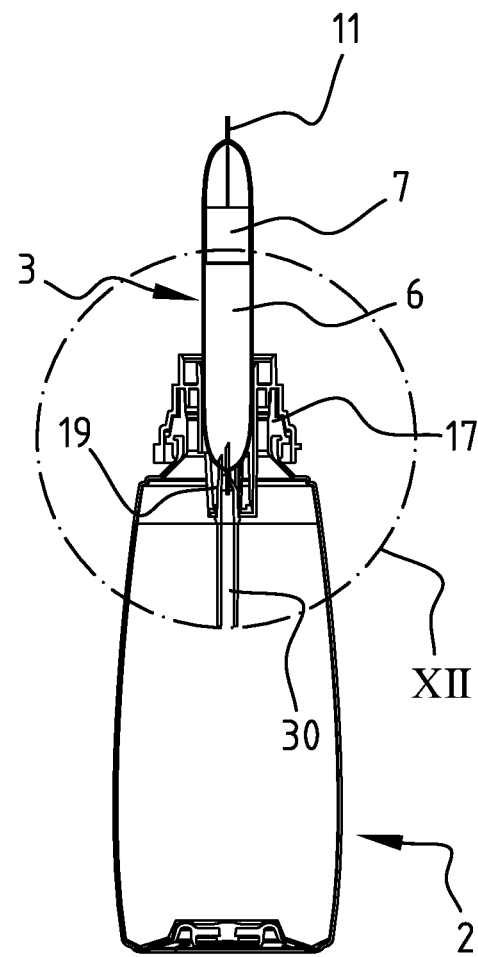
FIG. 10
FIG. 11 section XI-XI detail XII

SYSTEM AND METHOD FOR DISPENSING A MIXTURE OF A LIQUID AND AN ADDITIVE AND CARTRIDGE FOR USE THEREIN

CROSS REFERENCE TO RELATED APPLICATIONS

This is a national stage application filed under 35 U.S.C. § 371 of pending international application PCT/EP2019/082642, filed Nov. 26, 2019, which claims priority to Netherlands Patent Application No. 2022072, filed Nov. 26, 2018, the entirety of which applications are incorporated by reference herein.

BACKGROUND

The present invention relates to a liquid dispensing system for use in combination with exchangeable cartridges containing an additive to be mixed with a liquid to be dispensed. In particular, the invention relates to such a system in which non-refillable cartridges can be replaced after use. More specifically, the invention relates to a liquid dispensing system comprising at least one container for storing the liquid to be dispensed, the at least one container having a neck defining an fill opening for the liquid; a liquid dispensing device releasably connectable to the at least one container; an exchangeable cartridge for an additive to be mixed with the stored liquid, said cartridge being accommodated in the neck; and means for opening the cartridge. Such a liquid dispensing system is disclosed in the applicant's earlier international application PCT/EP2017/078516.

Nowadays consumer goods are increasingly bought on the internet. This applies not just to clothing, shoes and electronics, but also to day-to-day shopping. This development has implications for the design of products, which must lend themselves to being shipped in small quantities or even individually, possibly in combination with other types of goods. Moreover, since physical inspection of goods before purchase is not possible, and since no retailer is involved as link between the consumer and the manufacturer involved, it is increasingly important to ensure that products cannot be tampered with, so that the consumer gets the exact product that he has ordered.

Another challenge in product design nowadays is sustainability.

The above-identified application PCT/EP2017/078516 discloses a liquid dispensing system which comprises a container for storing the liquid to be dispensed and a liquid dispensing device which is releasably connectable to the container. The container has a neck in which a cartridge for an active liquid to be mixed with the stored liquid can be accommodated. The cartridge has an outflow opening to allow the active liquid to flow into the container, as well as an aerating opening to allow air in.

Providing a cartridge filled with active liquid as proposed in this earlier application allows an end user to obtain the liquid desired, e.g. a detergent, by simply filling the container with water and then mixing in the additive, e.g. a concentrate. In this way the volume of liquid to be shipped from producer to end user can be reduced dramatically. The cartridge is small enough to fit in a letterbox, which simplifies distribution since the cartridge can be sent by regular mail. And even if a courier service is engaged, the courier does not have to wait for someone to deliver the package to, but can simply put it in the letterbox.

The invention has for its object to provide a further improved liquid dispensing system that meets the demands of both e-commerce and sustainability. In accordance with the invention, this is achieved in the liquid dispensing system of the type defined above in that the cartridge comprises a one-piece hollow body filled with the additive and with a pressurized gas; and the opening means comprise at least one piercing member arranged to pierce a wall of the hollow body. By packing the additive together with a pressurized gas, the additive may be discharged from the cartridge easily and swiftly. Moreover, embodying the cartridge as a one-piece hollow body results in relatively little waste when the cartridge is discarded after use, while the cost of the cartridge will also be relatively low.

The term "one-piece" is intended to denote a body which has been integrally made, without any step of assembling and fixing separately made parts. A "piercing member" may be any sharp object which is suitable for forming an opening in the wall of the hollow body, including but not limited to a spike, a needle, a cutting blade, a sharpened edge, etc.

In one embodiment of the liquid dispensing system, the hollow body is substantially tubular and includes opposite end parts that are sealed. A tubular body is easy to handle, to store and to transport, and can easily be manufactured in one piece. Due to its shape it can further withstand internal gas pressure.

When the cartridge has an inner diaphragm extending from one end part to the other and separating the additive from the pressurized gas, it may be used for any combination of gas and additive, regardless of their characteristics.

In an embodiment of the liquid dispensing system, the hollow body may be made of a flexible material. The hollow body may be thin-walled, and may collapse after the pressurized gas has been released, so as to limit the volume of waste material after use.

In a further embodiment, the hollow body may be made of a plastics material. Plastics are easy to handle in manufacturing, can be made gas-tight and are low-cost. Moreover, plastics can be recycled after use. The hollow body may be made of several layers of plastics material, and may include various types or grades of plastics material, depending on the characteristics that are required of the cartridge, such as barrier characteristics, strength, resiliency, transparency or color, etc.

The container may include a support structure arranged in the neck and configured to hold the cartridge. Such a support structure allows the cartridge to be easily arranged in and removed from the neck of the container.

In order to allow the cartridge to be pierced upon being arranged in the container, the at least one piercing member may be arranged in or near the neck of the container.

This may be achieved in that the at least one piercing member is connected to the support structure.

When the cartridge is arranged to be inserted into the neck along a longitudinal axis and the at least one piercing member is arranged substantially parallel to the longitudinal axis, the force for piercing the cartridge may be derived from the insertion thereof.

In a further embodiment of the liquid dispensing system, the at least one piercing member is offset with respect to the longitudinal axis. In this way it is ensured that when piercing the wall of the hollow body the piercing member does not hit a welded part thereof.

In an embodiment of the liquid dispensing system, the at least one piercing member may be hollow and may have a cutting edge facing the cartridge and an outlet in fluid communication with an interior of the container. In this way the piercing member forms a conduit guiding the additive from the cartridge to the container.

The invention further relates to a method of dispensing a liquid, comprising the steps of: filling at least one container with the liquid to be dispensed; providing at least one exchangeable cartridge filled with an additive; arranging the cartridge in a neck of the container; opening the cartridge to allow the additive to flow into the container and mix with the liquid; and dispensing the stored liquid mixed with the additive. Such a method is also disclosed in PCT/EP2017/078516.

The invention has for its object to provide an improved method of this type. To that end the method of the invention is characterized in that: the cartridge comprises a one-piece hollow body filled with the additive and with a pressurized gas; opening the cartridge further includes piercing a wall of the hollow body by means of a piercing member; and allowing the additive to flow into the container includes forcing the additive through the pierced wall by means of the pressurized gas. As stated above, using the pressurized gas to force the additive out of the cartridge allows the contents of the cartridge to be emptied into the container swiftly and completely. Moreover, the force with which the additive is injected into the liquid facilitates mixing. And using a one-part hollow body as cartridge reduces material consumption and waste.

In an embodiment of the method according to any one of claims 12-17, characterized in that after the stored liquid mixed with the additive has been dispensed from the container, the cartridge is removed from the neck of the container and a new cartridge filled with additive and pressurized gas is arranged in the neck. In this way a new mixture may be formed in the liquid dispensing device.

To that end the container may be refilled with liquid to be dispensed before the new cartridge is arranged in the neck.

Further embodiments of the method are defined by the dependent claims 13-17.

And finally, the invention relates to a cartridge for use in a liquid dispensing system as disclosed above or in a method as discussed above.

BRIEF DESCRIPTION OF THE SEVERAL VIEWS OF THE DRAWINGS

The invention will now be illustrated by means of a number of exemplary embodiments thereof, wherein reference is made to the accompanying drawings, in which corresponding elements carry reference numerals incremented by "100", and in which:

FIG. 5 is a perspective view of the cartridge of FIGS. 3 and 4;

FIG. 6 is a cross-sectional view of the cartridge along the line VI-VI in FIG. 5;

FIG. 10 is a front view of the liquid dispensing system at the stage of assembly shown in FIG. 8;

FIG. 11 is a longitudinal sectional view of the container and cartridge along the line XI-XI in FIG. 10;

DETAILED DESCRIPTION

Figure 7:
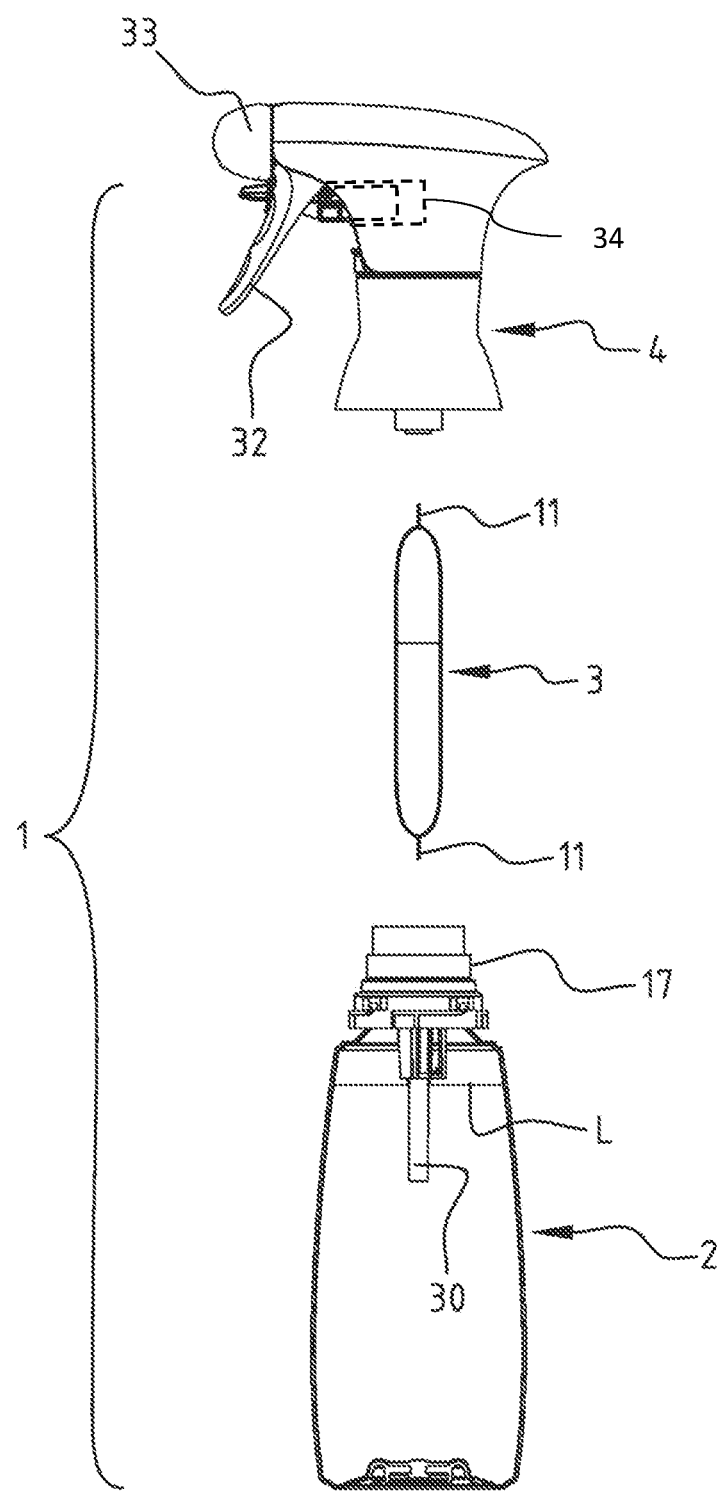
FIG. 7 is an exploded side view of an embodiment of the liquid dispensing system in accordance with the invention, including a container, a cartridge and a dispensing device, in which the container body is shown in longitudinal section.
Figure 8:
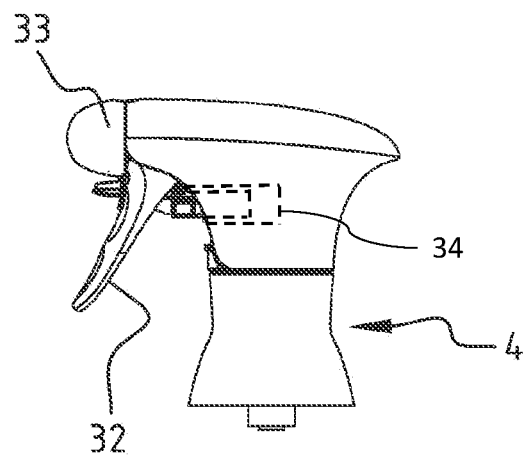
FIG. 8 is a view corresponding with FIG. 7 and showing the cartridge being introduced into the container.

A liquid dispensing system 1 in accordance with an embodiment of the invention comprises a container 2, a cartridge 3 and a dispensing device 4 (FIG. 7). The container may be a so-called "bag-in-bottle" container like the Flair® type containers marketed by the applicant.

Figure 1:
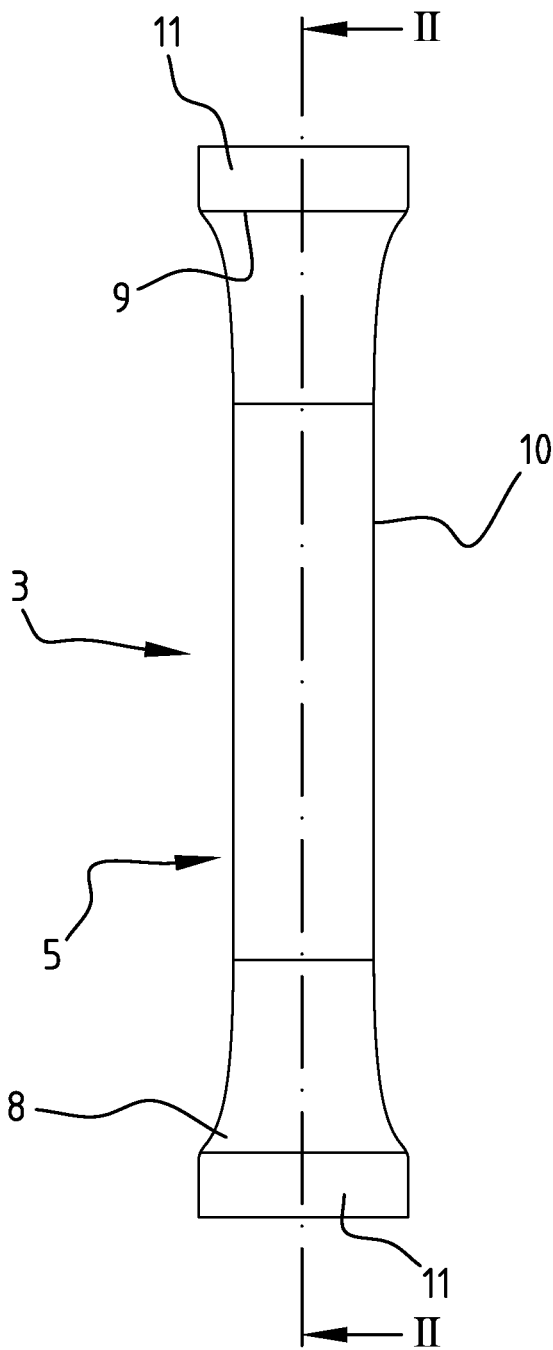
FIG. 1 is a front view of a first embodiment of a cartridge for use in a liquid dispensing system in accordance with the invention.
Figure 2:
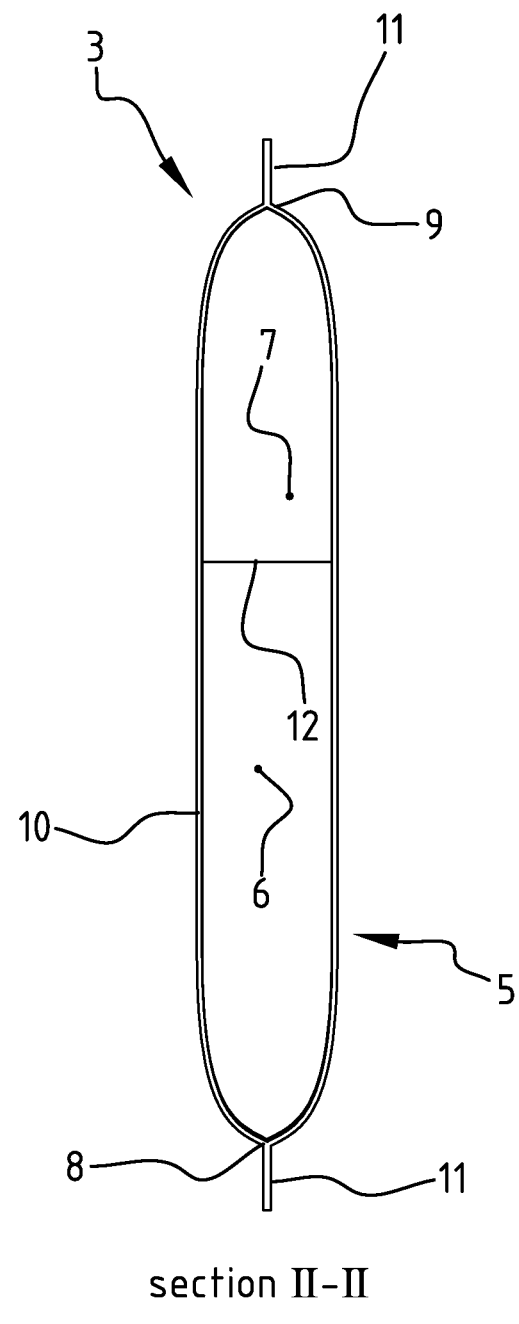
FIG. 2 is a longitudinal sectional view of the cartridge along the line II-II in FIG. 1.
Figure 3:
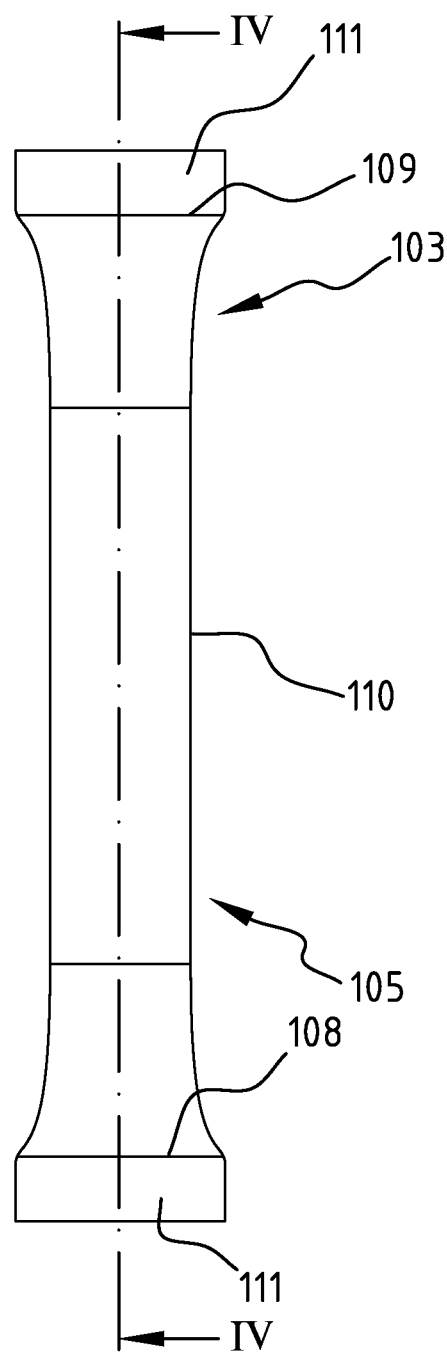
FIG. 3 is a front view of a second embodiment of the cartridge.
Figure 4:
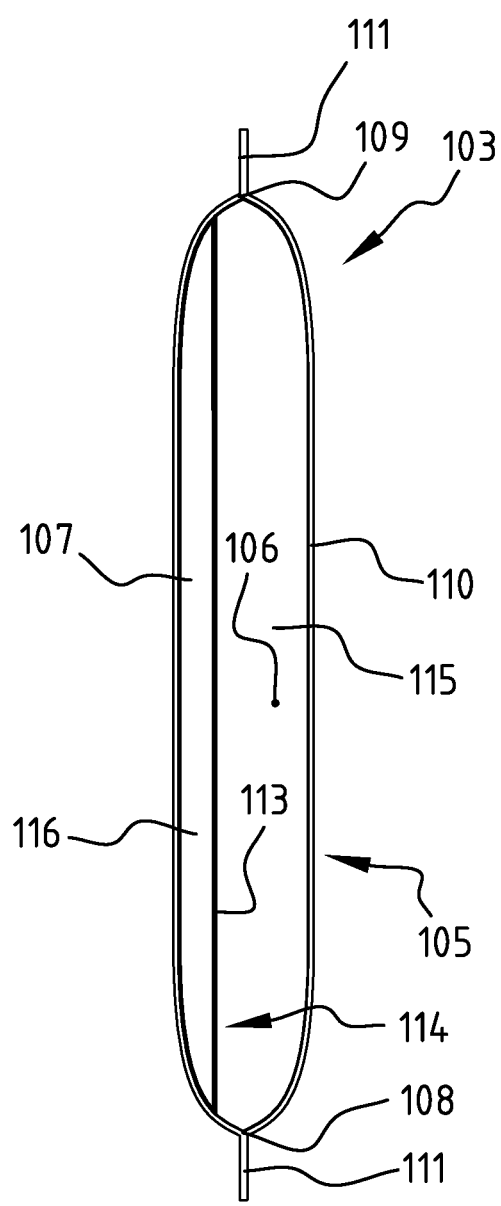
FIG. 4 is a longitudinal sectional view of the cartridge along the line IV-IV in FIG. 3.

In this embodiment the cartridge 3 comprises a one-piece hollow body 5 that is filled with an additive 6 and a pressurized gas 7 (FIG. 1). The additive 6 may be a liquid or a granular material, in particular a powder. The pressurized gas may be air or another gas. The gas, which merely serves as a propellant, is selected such that it does not react with or otherwise affect the additive, with which it is in direct contact at an interface 12.

In the illustrated embodiment the hollow body 5 is substantially tubular and has opposite ends 8, 9 which are sealed.

Such a tubular hollow body 5 may be manufactured by providing a tube 10 made from a plastics material, sealing it at a first end 8, filling the tube 10 with the additive and the pressurized gas and then sealing it at a second end 9 opposite the first end 8. The tube 10, which will form a single continuous wall of the hollow body 5, may be made from any suitable plastics material, and may include multiple layers made from different materials, such as e.g. PE, PP, EVOH, (functionalized) polyolefins, or any other material having suitable properties. The tube 10 may be made by extrusion, by injection molding or by rolling a sheet and welding it at the seam. When using injection molding the tube 10 could be formed with a closed bottom, like a test tube. In that case it could be filled straight away and would only have to be sealed at one end. The tube 10 may be sealed by a simple transverse weld 11, which will extend somewhat outside the tube 10 so that the width of the cartridge 3 is somewhat greater than the diameter of the tube 10.

Figure 13A:
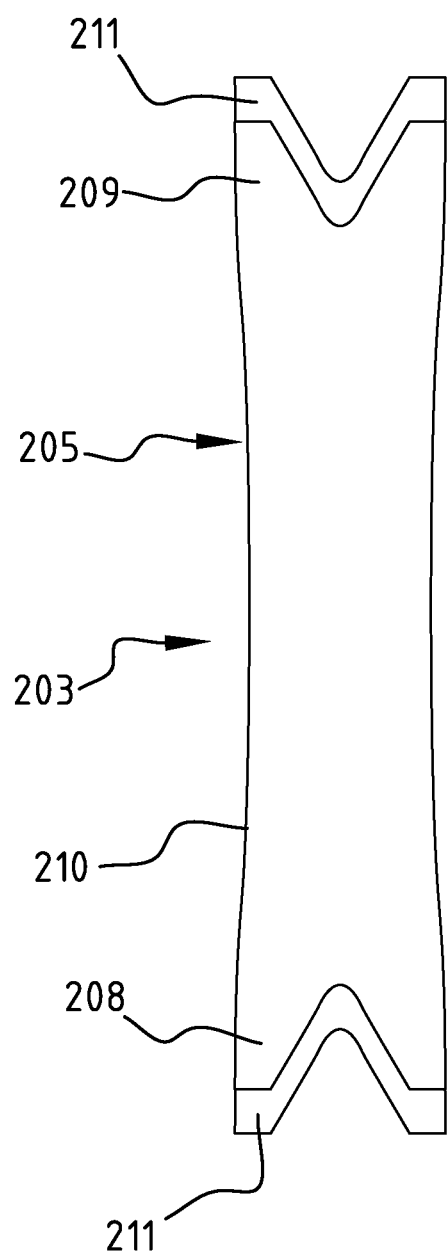
FIGS. 13A and B are front and side views, respectively, of a third embodiment of the cartridge.
Figure 13B:
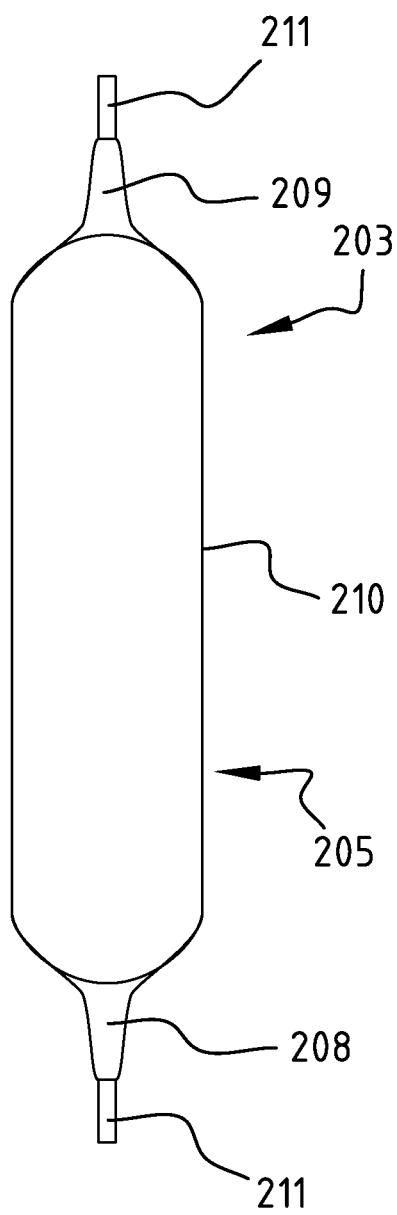

For applications where the diameter of the tube 210 should not be exceeded by the weld, e.g. because it is important that the tubular wall be supported by an external structure, a special V-shaped weld 211 may be formed (FIG. 13). This will cause a slight reduction in the useful volume of the hollow body 205, due to the inwardly directed shape of the weld 211.

Figure 14A:
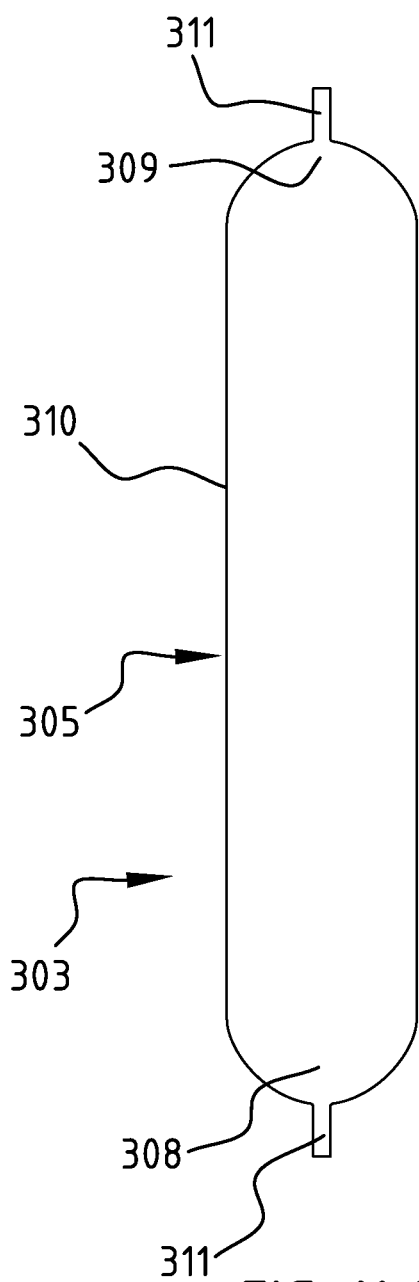
FIGS. 14A and B are front and side views, respectively, of a fourth embodiment of the cartridge.
Figure 14B:
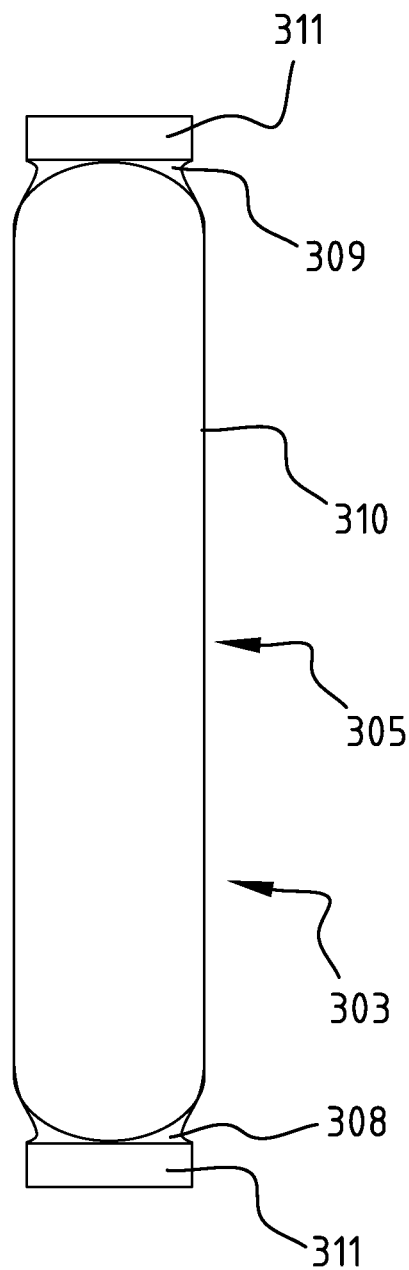

Another way to prevent the weld 311 from extending outside the tube 310 is by increasing the diameter of the tube 310, e.g. by filling it with gas at a relatively higher pressure (FIG. 14). In this way the maximum dimensions of the cartridge are defined by diameter of the pressurized tube 310, rather than the width of the weld 311.

For applications were the gas should not come into contact with the additive, a further embodiment of the cartridge 103 comprises a tubular hollow body 105 including an inner diaphragm 113. This diaphragm 113, which extends from one end part 108 to the other 109, separates the additive 106 from the pressurized gas 107. In the illustrated embodiment the diaphragm 113 forms part of an inner tube 114 which may be co-extruded or co-molded with the tube 110 forming the hollow body 105. Alternatively, this embodiment of the cartridge could be made by welding together three layers of foil or by separating a tube by means of a longitudinal weld line.

The diaphragm 113 separates the interior of the hollow body 105 into a first chamber 115 for the additive 106 and a second chamber 116 for the pressurized gas 107. The diaphragm 113 should be positioned such that when the cartridge 103 is opened, the second chamber 116 remains intact so that the pressurized gas 107 cannot escape. Otherwise the pressurized gas 107 could not act as a propellant for forcing the additive 106 out of the cartridge 103.

The container 2 may be filled with a liquid to be dispensed, e.g. water, to which the additive may be admixed before dispensing. The cartridge 3 is arranged to be accommodated in a neck 17 of the container 2. The additive may be released from the cartridge 3 by forming an opening the wall of the hollow body 5 using opening means 18. In accordance with the invention, the opening means 18 comprise a piercing member 19 arranged to pierce the wall of the hollow body 5. In this embodiment the piercing member 19 is hollow and has a cutting edge 20 facing the cartridge 3 and an outlet 21 in fluid communication with an interior of the container 2 (FIG. 12).

Figure 12:
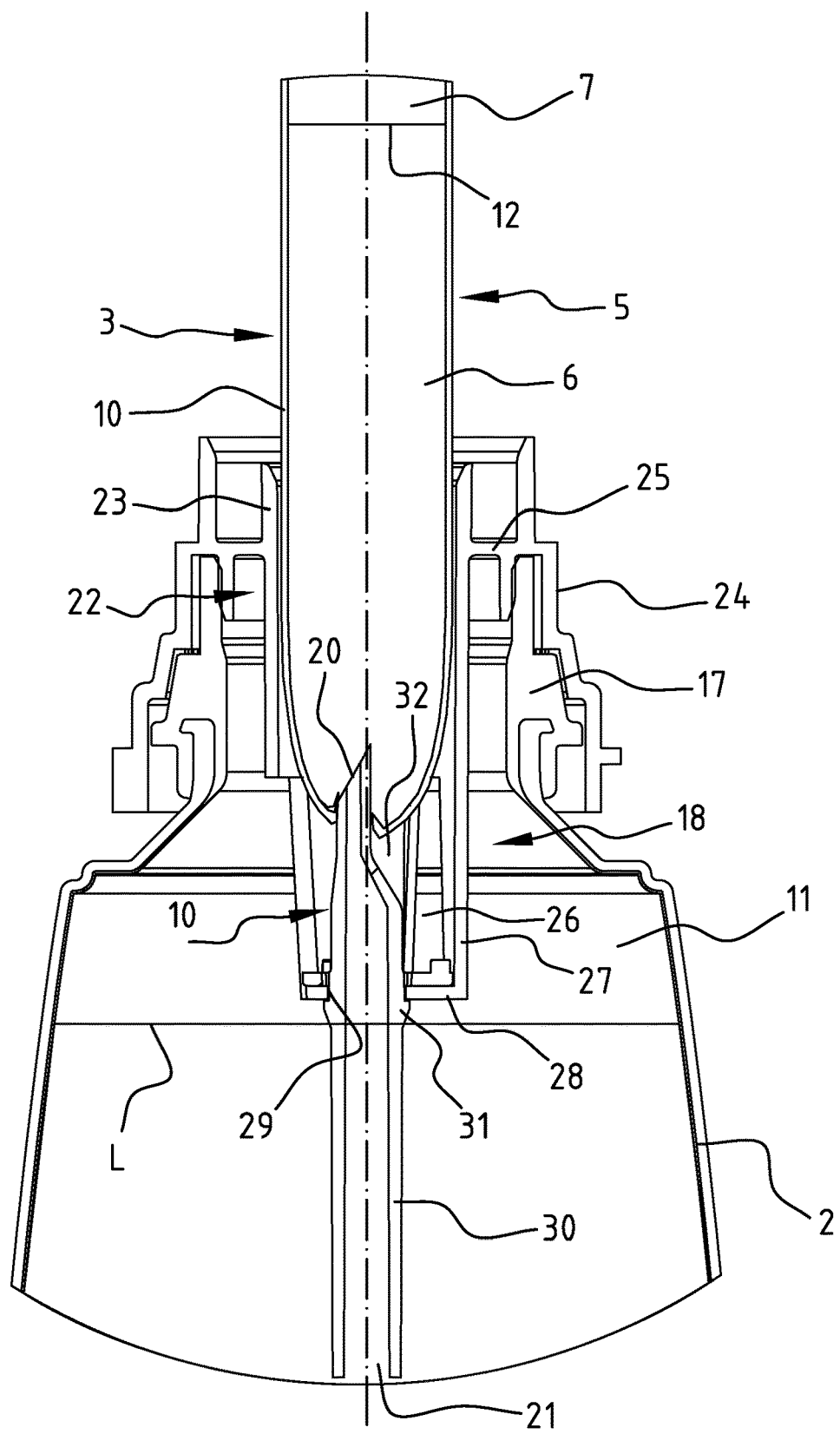
FIG. 12 is an enlarged scale detail view of the area enclosed by circle XII in FIG. 11.

As shown in FIG. 12, the container 2 includes a support structure 22 arranged in the neck 17 and configured to hold the cartridge 3. In this embodiment the support structure 22 is annular and includes an inner ring 23 which is connected to an outer ring 24 by a radial flange 25. The outer ring 24 is fixed to the neck 17 of the container 2. The inner ring 23 is dimensioned to accommodate the cartridge 3 with some play, so as to facilitate insertion of the cartridge into the neck 17. The inner ring 23 may include two opposite grooves (not shown in the side view of FIG. 12) for allowing the weld 11 at the lower end 8 of the cartridge 3 to pass.

In this embodiment the piercing member 19 is arranged in or near the neck 17 of the container 2 as well. In fact, the piercing member 19 is connected to the support structure 22. In the lower part of the support structure 22, which faces the interior of the container 2, the ring 23 has a number of recesses 26 dividing the ring 23 into separate arms 27, which are connected at their lower ends by a radial flange 28. This flange 28 has an opening 29 through which the piercing member 19 protrudes. The piercing member 19 is fixed by a shoulder 31 which abuts the flange 28. The recesses 26 allow additive which escapes from the hollow body 5 through the opening in the wall, but flows outside of the piercing member 19 to still reach the interior of the container 2.

The piercing member 19 has a tubular part 30 between its cutting edge 20 and the outlet 21. This tubular part 30 extends a limited distance into the interior of the container 2, below the level L of the liquid. In this way the tubular part 30 of the piercing member 19 acts as a short dip tube. This short "dip tube" serves to ensure that liquid is always dispensed, rather than air from a headspace H.

Between the tubular part 30 and the cutting edge 20 the piercing member 19 has a tapering part 32. This tapering part 32 is asymmetric, so that the cutting edge 20 is offset from a central axis of the tubular part 30, which coincides with a central axis C of the neck 17. Since the cartridge 3 is symmetrically arranged in the neck 17, this offset ensures that the cutting edge 20 does not engage the weld 11, which will normally lie within a symmetry plane of the hollow body. Instead, the piercing member 19 will hit the wall somewhere between the weld 11 and the tubular part 10, where it runs at an angle to the central axis C.

If the hollow body 5 is made in the shape of a test tube, which is possible with injection molding, then it will not have a lower weld. In that case the cutting edge 20 could be centrally located and there would be no need for the tapering part 32.

Figure 9:
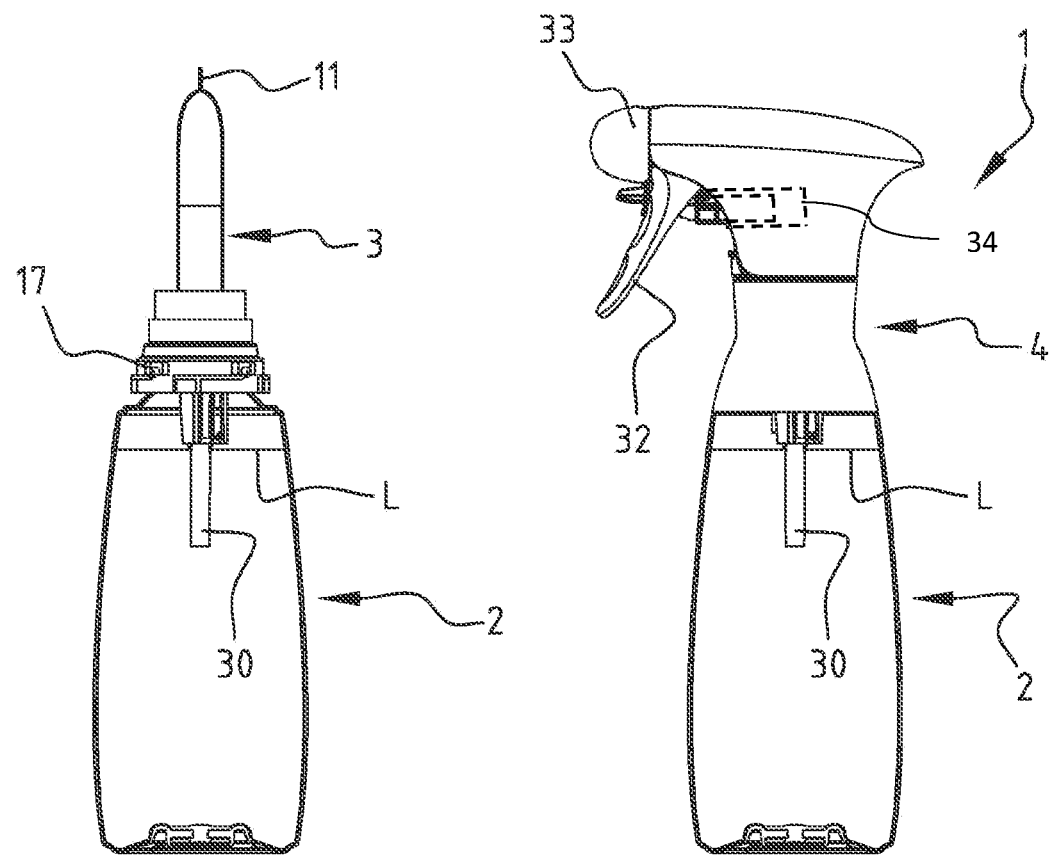
FIG. 9 is a view corresponding with FIGS. 7 and 8, showing the dispensing device mounted on the neck of the container.

Since the wall runs at an angle to the central axis C, while the cartridge 3 is inserted into the container neck 17 substantially parallel to the central axis or longitudinal axis, the cutting edge 20 will hit the wall at an angle. The closer the cutting edge 20 is to the weld 11, the greater the angle, which makes piercing the wall relatively easy. The wall may be pierced as soon as the cartridge 3 is inserted into the neck 17 of the container (i.e. the situation shown in FIGS. 8 and 10-12), but it is also conceivable for the cartridge to be arranged loosely in the upper part of the inner ring 23, and then to be pushed to the position shown in FIG. 12 only when the liquid dispensing device 4 is connected to the container (see FIG. 9).

Once the wall of the hollow body 5 has been pierced, the additive 6 will flow out of the hollow body 5 very quickly, due to the gas pressure acting on the additive. While the additive flows out through the opening in the wall and the tubular part 30 of the piercing member 19, air from the head space H of the container 2 enters the inner ring 23 from all sides and further serves to compress the empty hollow body 5. Since the hollow body 5 is opened by plastic deformation, i.e. by piercing its wall, it cannot be refilled. Consequently, after the cartridge 3 has been emptied and the liquid from the container 2 has all been spent, the empty cartridge 3 has to be replaced by a new cartridge filled with the additive.

In the illustrated embodiment the liquid dispensing device 4 is a sprayer head, which includes a pump 34 (see FIG. 7) actuated by a trigger 32 against the biasing force of a spring (not shown). The sprayer head includes a nozzle 33. The sprayer head may be a precompression sprayer including a precompression valve between the pump 34 and the nozzle, but may also be a conventional sprayer. Alternatively, the dispensing device 4 might even be a buffer type dispensing device like the Flairosol® that is marketed by the applicant. The dispensing device 4 can be connected to the container neck 17 by any conventional means, like e.g. a threaded connection, a bayonet connection or a 'snap-on, twist-off' connection. The necessary thread or bayonet elements can be arranged on the outside of the outer ring 24 of the support structure 22.

Once the container 2 has been filled with a first liquid, a cartridge 3 has been arranged in the neck 17 of the container 2 and the spray head or dispensing device 4 has been connected to the container neck 17, the liquid dispensing system 1 is ready for use. Arranging the cartridge 3 in the container neck 17 and/or connecting the dispensing device 4 to the neck 17 has caused the additive to be forcibly discharged into the container, where it has mixed with the first liquid. This mixture of the liquid stored in the container 2 and the additive stored under gas pressure in the cartridge 3 can be dispensed by actuating the trigger 32 of the dispensing device 4.

When all liquid has been dispensed from the container 2, the dispensing device 4 may be disconnected from the container 2. Subsequently, the empty cartridge 3 may be taken from the support structure 22 in the neck 17 of the container 2. The cartridge 3 cannot be used anymore and has to be replaced by a fresh cartridge 3.

Figure 15:
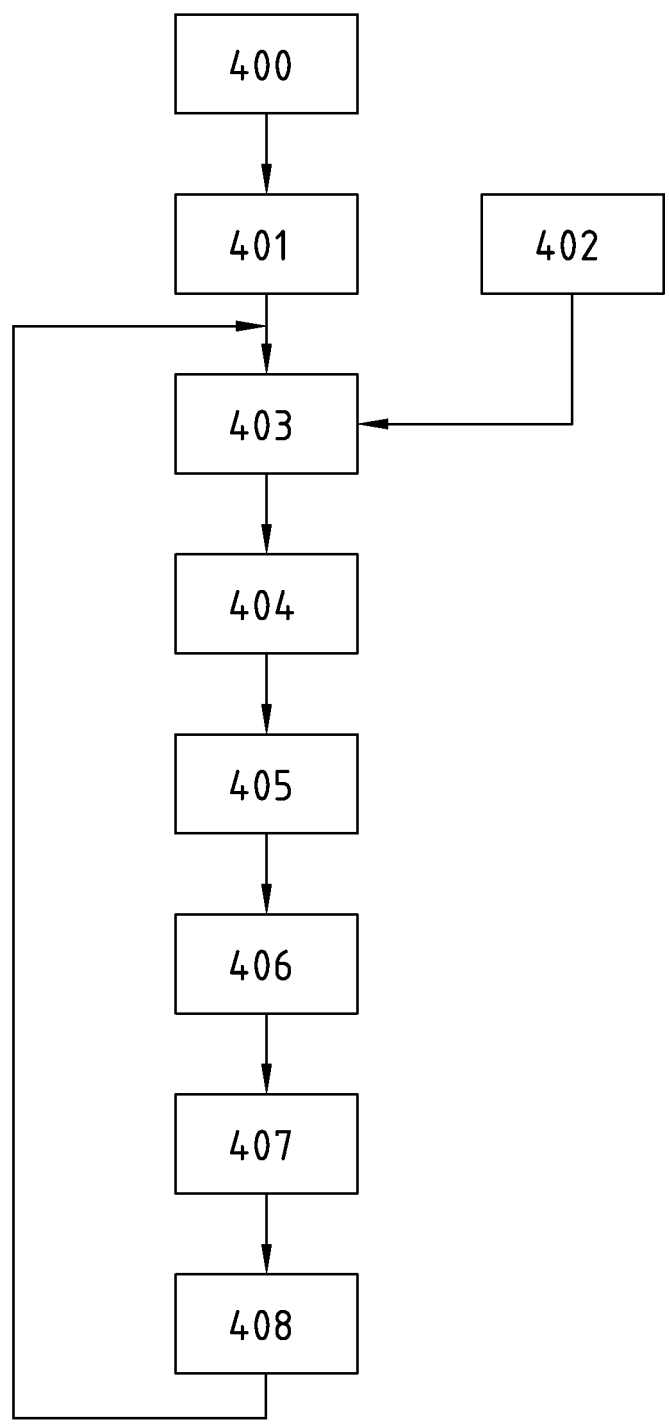
FIG. 15 is a flowchart showing the steps of an embodiment of the method of the invention.

The method is illustrated by the flow chart of FIG. 15.

In step 400 a container 2 is provided, which is filled with a liquid in step 401. In step 402 a cartridge 3 is provided, which is filled with an additive 6 and a pressurized gas 7. In step 403 the cartridge 3 is arranged in (the neck 17 of) the container 2. Step 404 sees the cartridge 3 being pierced by the piercing member 19, resulting in the additive 6 being forced out by the gas pressure and mixing with the liquid in the container. In step 405 the liquid dispensing device 4 is mounted on (the neck 17 of) the container 2. As explained above, steps 404 and 405 could be reversed, with the cartridge being pierced when the dispensing device is mounted on the container. Step 406 is the normal use of the liquid dispensing system to dispense the liquid mixture by operating the dispensing device 4. In step 407 the dispensing device 4 is disconnected from the container 2 after the liquid mixture has been completely dispensed—or if a user simply needs the system to dispense another liquid mixture. Once the dispensing device 4 has been disconnected the empty cartridge can be removed and discarded in step 408. Since the cartridge is a one-piece hollow body made (usually) of plastics material, it can simply be recycled as plastics waste. From step 408 the method returns to step 403, where a new cartridge 3 is arranged in the container 2.

In this way the invention provides a liquid dispensing system and method which allows a container and in particular a liquid dispensing device, which are the most expensive parts of the system, to be used more than once. The container and device may be used to dispense a liquid that is a mixture of a liquid stored in the container 2 and an additive stored in the cartridge 3. The additive may be a concentrate which is merely diluted by water present in the container, or it may be one component of a two-component liquid system, of which the other component is the liquid in the container. Since the cartridges are relatively small, they can be easily transported and sent around the world. Therefore, this liquid dispensing system is very well suited for e-commerce. Moreover, because of the fact that the main parts of the system are re-used, whereas the cartridges are relatively small and may be recycled, the carbon footprint of the system is small.

Although the invention has been described by way of some exemplary embodiments, it will be clear that many variations are conceivable in the scope of the appended claims.

The invention claimed is:

1. A liquid dispensing system comprising:
at least one container for storing a liquid to be dispensed, the at least one container having a neck defining a fill opening for the liquid;
a liquid dispensing device releasably connectable to the at least one container, the liquid dispensing device including a trigger actuated pump;
an exchangeable cartridge for an additive to be mixed with the stored liquid, said cartridge being accommodated in the neck; and
means for opening the cartridge;
wherein the cartridge comprises a one-piece hollow body filled with the additive and with a pressurized gas; and
wherein the opening means comprise at least one piercing member arranged to pierce a wall of the hollow body.

2. The liquid dispensing system according to claim 1, wherein the hollow body is tubular and includes opposite end parts that are sealed.

3. The liquid dispensing system according to claim 2, wherein the cartridge has an inner diaphragm extending from one end part to the other and separating the additive from the pressurized gas.

4. The liquid dispensing system according to claim 1, wherein the hollow body is made of a resilient material.

5. The liquid dispensing system according to claim 1, wherein the hollow body is made of a plastics material.

6. The liquid dispensing system according to claim 1, wherein the container includes a support structure arranged in the neck and configured to hold the cartridge.

7. The liquid dispensing system according to claim 1, wherein the at least one piercing member is arranged in or near the neck of the container.

8. The liquid dispensing system according to claim 7, wherein the container includes a support structure arranged in the neck and is configured to hold the cartridge, and the at least one piercing member is connected to the support structure.

9. The liquid dispensing system according to claim 7, wherein the cartridge is arranged to be inserted into the neck along a longitudinal axis and the at least one piercing member is arranged parallel to the longitudinal axis.

10. The liquid dispensing system according to claim 9, wherein the at least one piercing member is offset with respect to the longitudinal axis.

11. The liquid dispensing system according to claim 1, wherein the at least one piercing member is hollow and has a cutting edge facing the cartridge and an outlet in fluid communication with an interior of the container.

12. The cartridge for use in the liquid dispensing system according to claim 1.

13. A method of dispensing a liquid, comprising the steps of:
filling at least one container with the liquid to be dispensed;
providing at least one exchangeable cartridge filled with an additive;
arranging the cartridge in a neck of the container;
opening the cartridge to allow the additive to flow into the container and mix with the liquid; and
dispensing the stored liquid mixed with the additive;
wherein the cartridge comprises a one-piece hollow body filled with the additive and with a pressurized gas;
wherein opening the cartridge further includes piercing a wall of the hollow body by means of a piercing member;
wherein allowing the additive to flow into the container includes forcing the additive through the pierced wall by means of the pressurized gas; and
wherein dispensing the stored liquid mixed with the additive includes actuating a trigger of a trigger actuated pump of a liquid dispensing device connected to the container.

14. The method according to claim 13, wherein the wall of the hollow body is pierced when the cartridge is arranged in the neck of the container.

15. The method according to claim 13, wherein the wall of the hollow body is pierced when the liquid dispensing device is connected to the neck of the container.

16. The method according to claim 14, wherein the cartridge is inserted into the neck along a longitudinal axis and the hollow body is pierced in a direction parallel to the longitudinal axis.

17. The method according to claim 16, wherein the hollow body is pierced at a location which is offset with respect to the longitudinal axis.

18. The method according to claim 13, wherein allowing the additive to flow into the container includes allowing the additive to flow through the at least one piercing member from a cutting edge facing the cartridge to an outlet in fluid communication with an interior of the container.

19. The method according to claim 13, wherein after the stored liquid mixed with the additive has been dispensed from the container, the cartridge is removed from the neck of the container and a new cartridge filled with additive and pressurized gas is arranged in the neck.

20. The method according to claim 19, wherein the container is refilled with liquid to be dispensed before the new cartridge is arranged in the neck.

* * * * *